United States Patent [19]

Jenkins

[11] Patent Number: 5,352,457
[45] Date of Patent: Oct. 4, 1994

[54] TRANSDERMAL DEVICE

[75] Inventor: Anthony W. Jenkins, Comberton, United Kingdom

[73] Assignee: Ethical Pharmaceuticals Limited, Ely, United Kingdom

[21] Appl. No.: 30,265

[22] PCT Filed: Oct. 4, 1991

[86] PCT No.: PCT/GB91/01730
§ 371 Date: Apr. 5, 1993
§ 102(e) Date: Apr. 5, 1993

[87] PCT Pub. No.: WO92/05811
PCT Pub. Date: Apr. 16, 1992

[30] Foreign Application Priority Data

Oct. 5, 1990 [GB] United Kingdom ............ 9021674.8

[51] Int. Cl.$^5$ ............................................. A61F 13/02
[52] U.S. Cl. .................................... 424/448; 424/449
[58] Field of Search ................................ 424/448, 449

[56] References Cited

U.S. PATENT DOCUMENTS

| | | | |
|---|---|---|---|
| 4,031,894 | 9/1986 | Urquhart et al. | 128/268 |
| 4,746,509 | 5/1988 | Haggiage et al. | 424/449 |
| 4,769,028 | 9/1988 | Hoffmann | 424/443 |

FOREIGN PATENT DOCUMENTS

| | | |
|---|---|---|
| 0013606 | 7/1980 | European Pat. Off. . |
| 0156080 | 10/1985 | European Pat. Off. . |
| 0201828 | 11/1986 | European Pat. Off. . |
| 0209121 | 1/1987 | European Pat. Off. . |
| 0272562 | 6/1988 | European Pat. Off. . |
| 0272987 | 6/1988 | European Pat. Off. . |
| 0275716 | 7/1988 | European Pat. Off. . |
| 0279982 | 8/1988 | European Pat. Off. . |
| 0318385 | 5/1989 | European Pat. Off. . |
| 0328806 | 8/1989 | European Pat. Off. . |
| 0332010 | 9/1989 | European Pat. Off. . |
| 0371496 | 6/1990 | European Pat. Off. . |
| 2086224 | 5/1982 | United Kingdom . |
| 2146526 | 4/1985 | United Kingdom . |
| 2185187 | 7/1987 | United Kingdom . |
| 86/06281 | 11/1986 | World Int. Prop. O. . |
| 87/06144 | 10/1987 | World Int. Prop. O. . |
| 88/01497 | 3/1988 | World Int. Prop. O. . |
| WO8907959 | 9/1989 | World Int. Prop. O. . |

OTHER PUBLICATIONS

Patent Abstracts of Japan, vol. 12, No. 333 (C-526), Sep. 8, 1988.
Patent Abstracts of Japan, vol. 12, No. 159 (C-495), May 14, 1988.

*Primary Examiner*—D. Gabrielle Phelan
*Attorney, Agent, or Firm*—Bacon & Thomas

[57] ABSTRACT

The invention pertains to a method of preparing a device for transdermal delivery of an active ingredient which is solid at room temperature and in which part or all of the active ingredient is present in a saturated or supersaturated solution. In the first step, a mixture is prepared which includes at least a polymer adhesive, a vehicle for the polymer adhesive, an active ingredient and a solvent mixture for the active ingredient which solvent mixture comprises at least two solvents having different boiling points. The mixture is then formed into a film and dried. The vehicle for the polymer adhesive and at least one of the solvents and the solvent mixture have boiling points below the drying temperature of the film, while at least one of the solvents in the solvent mixture has a boiling point above the drying temperature of the film. Thus, at least one of the solvents remains in the film after drying and the solubility of the active ingredient contained in the remaining solvent is greater than 10%.

29 Claims, 3 Drawing Sheets

TRANSDERMAL DEVICE

The invention relates to a method of preparing a device for transdermal delivery of an active ingredient and to transdermal devices prepared by that method.

The administration of drugs through the skin is a concept which is now well established and this route has several advantages over more conventional forms of drug delivery such as injection or oral ingestion. A particular advantage is that transdermal drug delivery devices can provide a sustained and controlled release of the active ingredient over a prolonged period so that the resulting blood levels remain constant. This is in contrast to other forms of administration where surges of the agent occur in the bloodstream immediately after administration and then drop away rapidly until the next dose is given. In the case of oral administration the blood level is further influenced by contents of the intestines and therefore difficult to control. Transdermal administration permits direct access to the bloodstream without first passage through the gastrointestinal tract and liver and also without the inherent problems associated with injection such as risk of infection and need for sterile administration equipment.

Because of the advantage of transdermal administration, in recent years a very large number of devices have been developed and described for the transdermal administration of a variety of pharmaceuticals. The devices are usually in the form of a patch or plaster to be attached to the skin. Early devices such as for example, that described in U.S. Pat. No. 3,598,122 comprised a reservoir containing the active ingredient, either in solid or liquid form. The reservoir walls were composed of a material permeable to that ingredient and it was stuck to the skin by a thin layer of adhesive which was also permeable to the active ingredient. The outer surface of the reservoir was covered with a backing material impermeable to the active ingredient. Such devices were bulky and solvents in which the active agent was dissolved tended to interfere with the ability of the adhesive to stick to the skin.

With improvements in adhesives available it was soon found possible, and indeed preferable, to prepare transdermal devices in which the adhesive layer itself provided the drug reservoir. Thus more modern transdermal devices usually comprise at least an impermeable backing material, a layer of drug-containing adhesive attached to the backing material and a release liner on the other adhesive surface which is removed for application of the device to the skin. Additional membranes are sometimes included within the device to regulate the rate of passage of the active agent from the adhesive to the skin.

Various methods have been used to achieve suitable drug/adhesive mixtures in which the active ingredient is dispersed in the adhesive without affecting the ability of the adhesive to stick to the skin. One of the earliest drugs to be administered by a transdermal device was nitroglycerin which is used in the treatment of angina pectoris and congestive cardiac failure. Nitroglycerin is well absorbed by the skin and therefore particularly amenable to transdermal administration. Conveniently it is a liquid at room temperature and so the approach that has been taken is to absorb it on to a solid such as lactose which is then dispersed in a polymer adhesive. Such devices are described in, for example U.S. Pat. No. 4,776,850, G.B. 2,081,582, and others. One or more other "solvents" are sometimes present in the nitroglycerin adhesive mixtures either as permeation enhancers, or for the purpose of "solvent casting" the mixture onto a backing layer.

Where the active ingredient to be incorporated into a transdermal device is a solid any solvent for the agent must be carefully chosen to be compatible with the adhesive. In WO86/00814 for example the problem is overcome by choosing a single solvent which is both a solvent for the drug and a solvent for the adhesive. However such a method restricts severely the number of different drugs which are compatible with a particular adhesive and also the type of adhesive which can be used.

Alternative methods have therefore been used in which a drug/adhesive mixture is prepared which includes a solvent for the drug and a solvent for the adhesive. The mixture is spread onto an appropriate backing material and then dried to evaporate the solvents leaving the drug dispersed in the adhesive in particulate form. A variation of the method is described in WO89/07951 in which the solvents for the adhesive are evaporated during a drying stage leaving the drug, in this case oestrogen, dispersed in particulate form in very high boiling point solvents which do not significantly evaporate on drying but which have a low capacity for the drug.

While the active ingredient can be taken up by the skin from a dispersion of the solid compound, the rate of uptake can be far better controlled if the agent is in a supersaturated solution, particularly where the solvent has an adequate capacity for the active ingredient. As the ingredient is taken up by the skin more will become dissolved in solution so maintaining a concentration gradient over a prolonged period which drives uptake through the skin. Transdermal devices are known which contain saturated drug solutions. They are described for example in G.B. 2,156,215 and U.S. Pat. No. 4,201,211. However these documents fail to describe a way in which the level of saturation can be precisely controlled to produce a supersaturated solution.

The present invention provides an improved method for preparing transdermal devices which contain supersaturated solutions of an active ingredient within an adhesive layer by use of a carefully selected mixture of solvents and selective evaporation of a particular solvent or solvents by drying at a temperature above the boiling points thereof, to influence the final concentration of the solution of active ingredient in the device.

In accordance with the invention a method of preparing a device for transdermal delivery of an active ingredient which is a solid at room temperature and in which part or all of the active ingredient is present in a supersaturated solution comprises the steps of:

(a) preparing a mixture comprising at least
  (i) a polymer adhesive
  (ii) a vehicle for the polymer adhesive
  (iii) the active ingredient
  (iv) a solvent mixture for the active ingredient which comprises at least two solvents;
(b) forming the mixture prepared in step (a) into a film, and
(c) drying the film prepared in step (b) wherein the vehicle for the polymer adhesive and at least one of the solvents in the solvent mixture for the active ingredient have boiling points below the drying temperature and at least one of the solvents in the solvent mixture for the active ingredient has a boiling point above the drying temperature and wherein the solubility of the active ingredient in the said solvent or solvents having a boiling point above the drying temperature is greater than 10%.

The above method provides a very precise way of preparing an adhesive/active ingredient mixture which contains a supersaturated solution of the ingredient after drying.

It is to be understood herein that the term "active ingredient" is intended to mean a single active agent or a combination of more than one active agent.

Dissolving the active ingredient in a mixture of solvents and then drying at a temperature which facilitates the evaporation of the vehicle for the adhesive and one of the solvents for the active ingredient, because it is above their boiling points, leaves the active ingredient in a supersaturated solution in the solvent or solvents that remain. Supersaturated solutions are particularly advantageous from the point of view of transdermal administration because they assist in controlling the rate of migration of the active ingredient through the skin as previously mentioned.

The choice of particular solvents, adhesives and drying temperatures is dictated by the solubility of the particular active ingredient in the solvent or solvents remaining in the device after drying. Thus with careful selection of all the components the method of the invention can provide transdermal devices which can administer a very wide range of drugs. The solubility of the active ingredient in the solvent or solvents having a boiling point above the drying temperature needs to be greater than 10%.

The polymer adhesive may be a polyisobutylene or silicone adhesive although acrylate polymer adhesives are particularly preferred. Suitable vehicles for the acrylate adhesives are for example methanol, ethanol, industrial methylated spirits (IMS), isopropanol and water. Suitable vehicles which may be used with polyisobutylene are toluene, xylene and methylene chloride. Suitable vehicles for silicone adhesives are chlorofluorocarbons such as, for example, trichlorotrifluoroethane. For acrylate adhesives aqueous dispersions are preferred. In this latter case drying temperatures used in drying the film must always be in excess of 100° C. at normal atmospheric pressures. Where the vehicle for the adhesive is a lower boiling solvent such as methanol (bp 65° C.), ethanol (bp 78.5° C.) or isopropanol (bp 82.4° C.), a lower drying temperature may be used providing it is above the boiling point of the low boiling solvent included in the solvent mixture for the active ingredient.

In one embodiment of the invention the vehicle for the adhesive and the solvent to be evaporated during drying from the solvent mixture for the active ingredient both are chosen to have a boiling point below that of ethanol. A drying temperature can thus be chosen which allows the ethanol to be maintained within the device. This is advantageous because ethanol is a useful skin permeation enhancer for some drugs. For acrylate systems a suitable solvent which may be evaporated while ethanol is retained is methanol. For non-aqueous systems ether or chlorofluorocarbons may be used.

In another embodiment of the invention the solvent in the solvent mixture for the active ingredient which is evaporated on drying may be ethanol, isopropanol, industrial methylated spirits (IMS) or water.

High boiling point solvents suitable for forming the saturated or supersaturated solutions of the active ingredient in the transdermal device are those having boiling points in excess of 110° C. Preferred solvent mixtures include one or more of diethylene glycol, propylene glycol, propylene carbonate, glycerol, lower molecular weight polyethylene glycols, propylene glycol esters, polyol fatty acid esters, fatty alcohol derivatives, oleic acid, iso-octyl stearate, iso-propyl myristate, isopropyl palmitate, ethyl oleate, diisopropyl adipate, diethylsuccinate, hexylaurate, triglycerides of caprylic or capric acids, diethyltoluamide, laurocapram, n-methylpyrrolidone and diethylene glycol monoether. Also suitable as solvents which are not evaporated from the device on drying are essential oils such as eucalyptus oil, tea-tree oil and lavender oil. Preferably at least one of the solvents which remains in the device will also act as a permeation enhancer to assist uptake by the skin of the active ingredient. Preferred solvent systems are propylene glycol-diethyltoluamide, n-methylpyrrolidone-diethyltoluamide, propylene glycol - diethylene glycol monoethyl ether and diethyltoluamide-diethylene glycol monoethyl ether - tea tree oil.

Among the active agents which may be included in transdermal devices produced by the method of the invention are anti-histamines such as, for example, clenastine fumarate, steroid hormones such as oestradiol, progestins such as norethisterone acetate, norgestrel, ethynodiol diacetate, medroxy progesterone acetate, gestodene and desogestrel, vasodilators such as nifedipine and diltiazem, antihypertensives such as clonidine and propranolol, bronchodilators such as salbutamol and clenbuterol, anti-tumour agents such as methotrexate and 5-fluouracil, alkaloids such as physostigmine and analgesics such as fentanyl, sufentanil, buprenorphine and hydromorphone. The device may contain an active ingredient which is a combination of more than one of the above active agents, for example an oestrogen with a progestin.

While the solvents to be used in the method of the invention must be selected in order that a supersaturated solution is produced on drying, solvents may also be selected which modify the properties of the adhesive so that it possesses the required degree of adhesion and tackiness to stick to the skin for the required period, which could be several days, but at the same time can be easily removed as required. The method of the present invention allows polymer adhesives which are normally too aggressive to be used in transdermal devices to be rendered suitable by choice and incorporation of an appropriate solvent mixture.

The assembly of a transdermal device prepared in accordance with the method of the present invention will now be described by way of example with reference to FIGS. 1 and 2 of the accompanying drawings and Examples 1 to 4.

Figure 1:
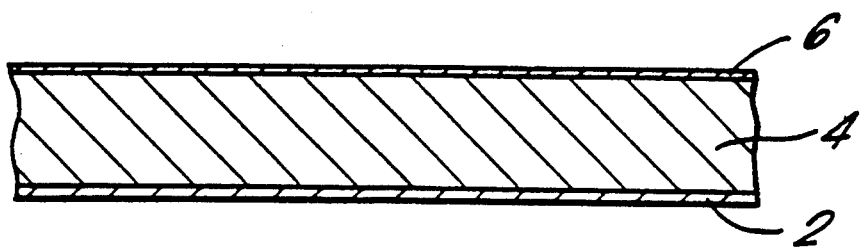
FIG. 1 is a vertical section through a first embodiment of the invention without the inclusion of a rate control membrane.

As already described, a mixture is formed which comprises a polymer adhesive in a suitable vehicle, the active ingredient to be administered, and a solvent mixture for the active ingredient which comprises at least two solvents one of which must have a boiling point above the drying temperature and one below. Preferably the active ingredient is first dissolved in the solvent mixture and the solution slowly added to the adhesive polymer previously dispersed in a suitable vehicle. Depending on the coating technique and adhesive used the addition of an adhesive thickener may be required. The mixture of adhesive polymer and active ingredient is formed into a film, preferably by coating onto a flexible sheet material. A typical embodiment of a device formed in accordance with the method of the invention is shown in FIG. 1. The adhesive mixture is formed into a layer 4 on a siliconised release paper 2. The layer is preferably about 5 to 500 μm thick. The coated release paper is dried at the appropriate temperature to drive off the necessary solvents and then laminated to a backing material 6 impermeable to the active ingredient. Suitable siliconised release liners are 3M Health Care Type 660 or 1360, Daubert HDPE 164Z or L. Stace types 635/6. Preferable backing materials include polyester film laminate (e.g. 3M Health Care Type 1012 or 1220), metalised polyester laminate (e.g. 3M Health Care Type 1109) and co-extruded high barrier films either clear (e.g. BXL Plastics Hybar) or skin-tone (e.g. Grace- Cryovac MF200). Backings having higher oxygen and water vapour transmission rates are preferred for devices intended for treatment for more than 24 hours. A suitable backing material in these circumstances is Semex polyester-urethane film type MF 4387-00.

The reverse manufacturing method is also possible and in some cases advantageous i.e. spreading the adhesive/solvent mixture onto the backing material and then laminating it to the release liner.

Figure 2:
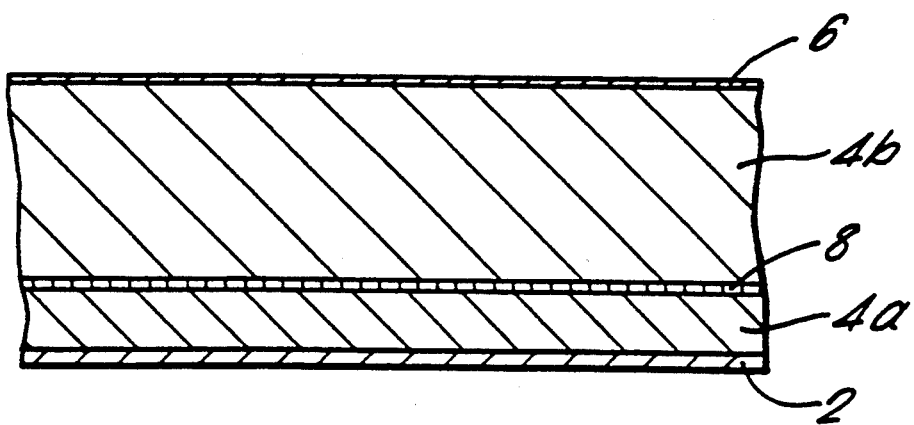
FIG. 2 is a vertical section through a second embodiment of the invention including a rate control membrane.
Figure 3:
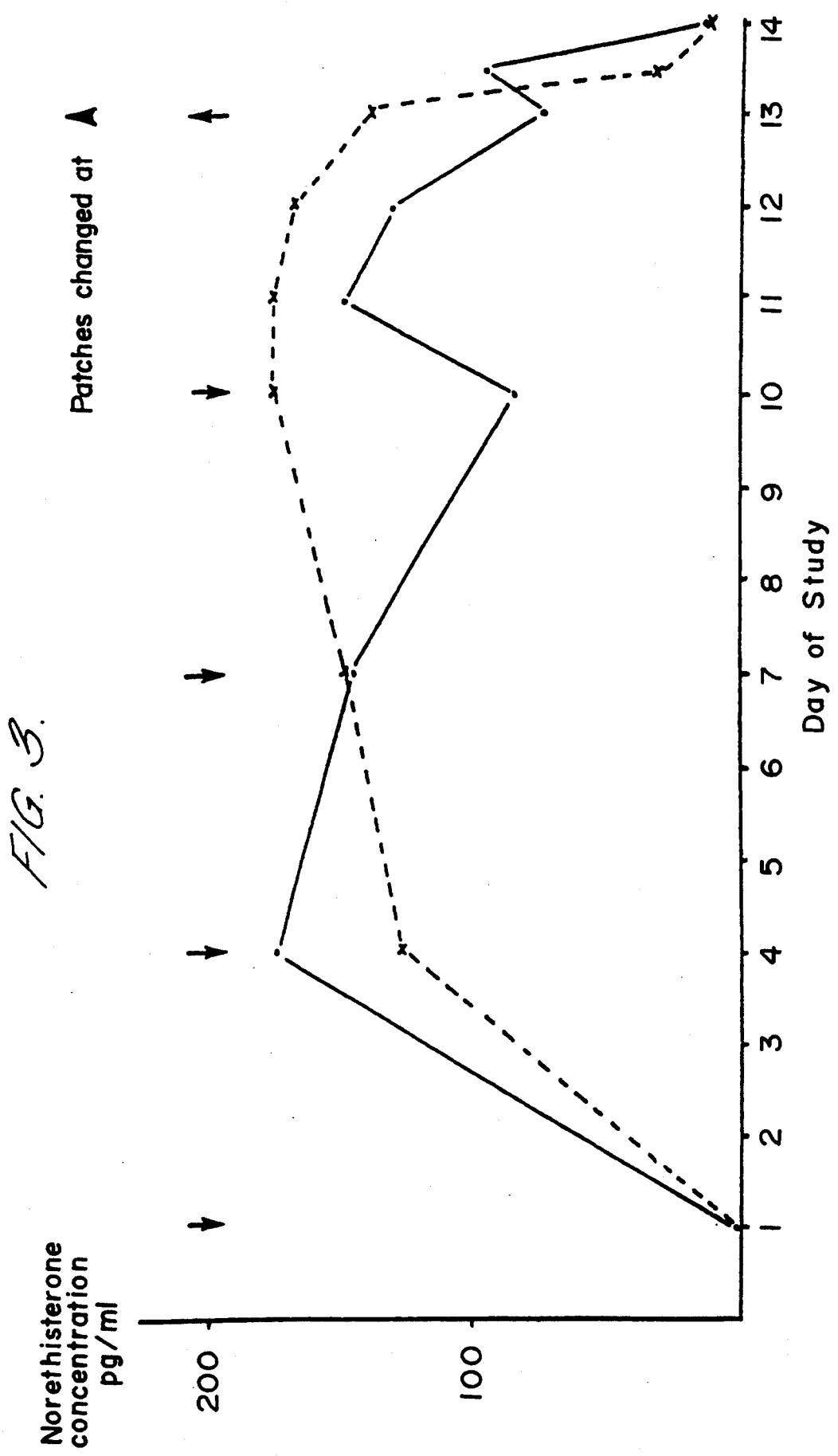
FIG. 3 shows mean plasma concentration time curves following transdermal administration of norethisterone acetate to four post menopausal women using a transdermal device prepared in accordance with the method of the invention ------. results from samples assayed by RIA at Liverpool University. x-----x results from same samples assayed by RIA at Hammersmith Hospital. ↑ transdermal patches applied or replaced. ↓ transdermal patches removed.

FIG. 2 shows a second embodiment of the invention in which the adhesive/active ingredient layer is divided by a rate control membrane 8. The layer 4a which, in use, is in direct contact with the skin provides an initial loading dose of the active ingredient. As this migrates into the skin the consequent concentration difference between layer 4a and 4b causes the layer 4a to be replenished with active ingredient from the layer 4b at a rate dictated by the rate control membrane. Thus the inclusion of such a membrane provides a further means to control the rate of uptake for a pre-determined period, firstly by selection of the appropriate membrane and secondly by varying the thickness of the layers 4a and 4b on either side of the membrane. Suitable materials for forming the rate control membrane include polypropylene film (e.g. Celgard microporous film), polyvinyl acetate film (e.g. Mowiol film (Hoechst) and ethyl vinyl acetate film (e.g. controlled caliper MSP series films obtained from 3M Health Care Speciality Division). The thickness of the layer 4a may be in the range 5 to 50 μm and the thickness of the layer 4b may be in the range 50 to 500 μm.

The device of FIG. 2 is formed as previously described except that when using conventional coating/drying equipment the process becomes two stages. The backing material 6, coated with adhesive layer 4b is laminated to rate control membrane 8. The second stage is the lamination of this laminate to the adhesive layer 4a which has been coated on to the release paper 2. Alternative manufacturing methods are possible and more than one rate control membrane can be incorporated at any location within a multilayer device. Preferably all of the above described layers are assembled on a single large sheet which is die cut into transdermal devices of the appropriate size.

EXAMPLE 1

Transdermal Device Containing Norethisterone Acetate Without A Rate Control Membrane A mixture of acrylate polymer adhesive and the active ingredient norethisterone acetate is formed containing the following:

| Component | Quantity (g) |
| --- | --- |
| Norethisterone acetate (micronised) | 395 |
| Propylene glycol | 2125 |
| Diethyltoluamide | 1000 |
| Ethanol (95%) or IMS | 1500 |
| Primal N560 (acrylate adhesive dispersion in water) | 44500 |
| Acrysol ASE 60 (thickener for adhesive diluted 50:50) | 480 |
| Total | 50 Kg |

The norethisterone acetate is dissolved in propylene glycol, diethyltoluamide and ethanol by sonication or warming. This solution is added slowly to the aqueous acrylate adhesive dispersion (Primal N560, Rohm & Hass) with mixing. An adhesive thickener (Acrysol ASE 60) is then added to the mixture as a 50% solution/water mix sufficient to produce a thicker spreading solution of around 800 cP (Brookfield) for reverse roll coating or 60,000 cP to suit knife over roll coating.

The mixture is coated on the backing polyester (3M Health Care Type 1109) at about 100 μm wet coating thickness and dried at about 105° C. to drive off the water and the ethanol or IMS from the acrylate adhesive. The resulting dried adhesive layer is about 55 μm thick. The release liner (Stace type 636) is laminated to the adhesive layer. The final sheet is die-cut to form transdermal devices of about 19 or 28.5 $cm^2$ each containing 1.5 or 2.25 mg norethisterone acetate respectively, which are packaged individually.

EXAMPLE 2

Transdermal Device Containing Oestradiol With Rate Control Membrane

A mixture is prepared containing the following:

| Component | Quantity (g) |
| --- | --- |
| 17β Oestradiol | 87.5 |
| Propylene glycol | 400 |
| Diethyltoluamide | 100 |
| 95% Ethanol or IMS | 100 |
| Polysorbate 20 | 12.5 |
| Primal N560 (acrylate adhesive dispersion) | 4262.5 |
| Acrysol ASE 60 (thickener for adhesive) 50:50 water | 37.5 |

-continued

| Component | Quantity (g) |
| --- | --- |
| Total | 5000 g |

The oestradiol is dissolved in the solvent mixture and slowly added to the aqueous adhesive to which an Acrysol ASE 60 thickener is also added in a similar way to Example 1. The mixture is coated onto a siliconised release liner (3M Health Care Type 660) to give a 50 μm wet coating which is dried at 105° C. as described above. When dried the adhesive layer and liner are laminated to a rate control membrane sheet material (3M ethyl vinyl acetate membrane, MSP 987192) which is then coated with a 250 μm wet coating of the same adhesive mixture and dried as before. The adhesive layers are then laminated to the clear polyester film laminate backing material as described. The sheets are cut into 20 cm² transdermal devices each containing 10.5 mg oestradiol and individually packaged for use.

EXAMPLE 3

Transdermal Device Containing Oestradiol Without A Rate Control Membrane

A mixture is prepared containing the following:

| Component | Quantity (g) |
| --- | --- |
| 17β oestradiol | 440 |
| Diethyltoluamide | 2250 |
| Isopropanol | 60 |
| Primal N560 | 47000 |
| Acrysol ASE 60:water (50:50) | 250 |
| Total | 50 Kg |

The devices are prepared and assembled as described in Example 1. The release liner is coated to a wet-coat thickness of 100 μm and after drying and laminating the laminate is die cut to 28.5 cm² devices each containing 2.5 mg oestradiol.

EXAMPLE 4

Transdermal Device Containing Oestradiol Without A Rate Control Membrane

A mixture is prepared containing the following:

| Component | Quantity (g) | |
| --- | --- | --- |
| 17-β Oestradiol (micronised) | | 30 |
| Diethyltoluamide | | 100 |
| Dioctylsodium sulphosuccinate | | 3 |
| Isopropanol/water 50:50 | | 2 |
| Primal N560 | | 655 |
| Primal N582 | | 200 |
| Acrysol ASE 60:water 50:50 | q.s | 10 |
| Total | | 1000 g |

Figure 4:
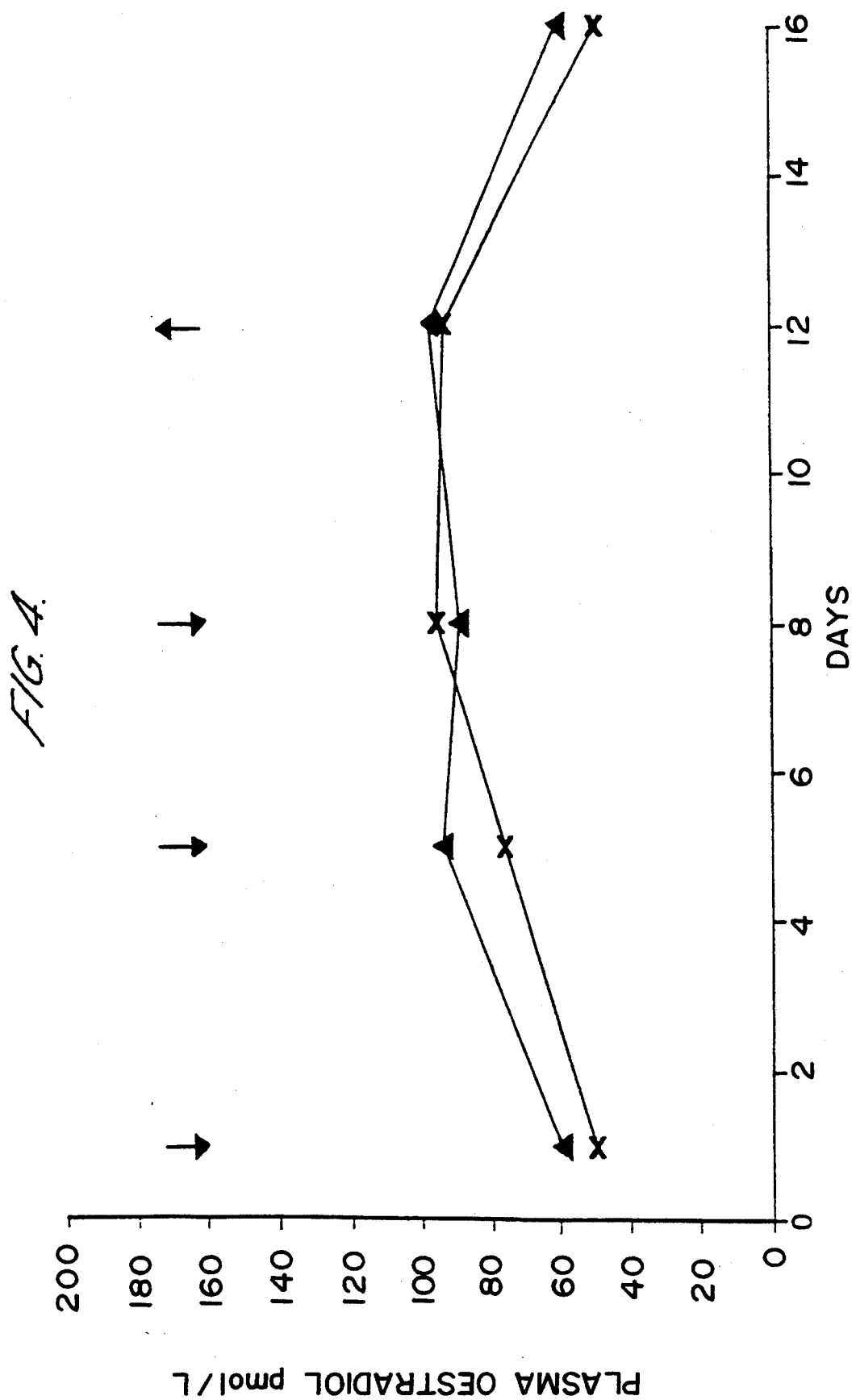
FIG. 4 shows mean plasma concentration time curves following transdermal administration of oestadiol using the devices of Example 4 (▲—▲) and known product Estraderm 50 (X—X). The arrows indicate patches applied, replaced or removed as above.

The devices are prepared and assembled as described in Example 1 except that the devices are cut to 20 cm². Results obtained in a 4 subject pharmacokinetic study in comparison with an existing product (Estraderm 50) are shown in FIG. 4.

EXAMPLE 5

Transdermal Device Containing Buprenorphine Without A Rate Control Membrane

A mixture is prepared containing the following:

| Component | Quantity (g) |
| --- | --- |
| Buprenorphine | 42 |
| Ethanol or IMS | 100 |
| Diethyltoluamide | 150 |
| Diethylene Glycol Monoethyl ether | 150 |
| Tea Tree oil | 100 |
| Primal N560 | 3908 |
| Primal N582 | 500 |
| Acrysol ASE 60:water 50:50 | 50 |
| Total | 5000 g |

The devices are prepared and assembled as described in Example 1 except that the release liner is coated to a wet coat thickness of 150 μm and after drying the laminate is cut to 20 and 50 cm² devices containing 2.5 mg/20 cm² or 6.3 mg/50 cm² buprenorphine respectively.

It is to be noted that the terms Hybar, Cryovac, Celgard, Mowiol, Contran, Primal, Acrysol, Brookfield, Triton and Estraderm, used in the specification are Registered Trade Marks.

I claim:

1. A method of preparing a device for transdermal delivery of an active ingredient which is a solid at room temperature and in which part or all of the active ingredient is present in a supersaturated solution comprising the steps of:
    (a) preparing a mixture comprising at least:
        (i) a polymer adhesive which is selected from the group consisting of acrylate polymer adhesives, polyisobutylene adhesives, and silicone adhesives;
        (ii) a vehicle for the polymer adhesive, which vehicle is selected from the group consisting of water, ethanol, industrial methylated spirits, isopropanol, toluene, xylene, methylene chloride, and chlorofluorocarbon;
        (iii) the active ingredient;
        (iv) a solvent mixture for the active ingredient which comprises at least two solvents having different boiling points;
    (b) forming the mixture prepared in step (a) into a film, and
    (c) drying the film prepared in step (b),
    wherein the vehicle for the polymer adhesive and at least one of the solvents in the solvent mixture for the active ingredient have boiling points below the drying temperature, and at least one of the solvents in the solvent mixture for the active ingredient has a boiling point above the drying temperature, and wherein the solubility of the active ingredient in the said solvent or solvents having a boiling point above the drying temperature is greater than 10%.

2. A method as claimed in claim 1 wherein the vehicle for the polymer adhesive is a solvent having a boiling point below that of ethanol.

3. A method as claimed in claim 2 wherein the vehicle for the polymer adhesive is methanol.

4. A method as claimed in claim 1 wherein the vehicle for the polymer adhesive is water.

5. A method as claimed in claim 1 wherein the solvent in the solvent mixture for the active ingredient with a boiling point below the drying temperature is selected from the group consisting of ethanol, industrial methylated spirits, isopropanol and water.

6. A method as claimed in claim 2 wherein the solvent in the solvent mixture for the active ingredient with a boiling point below the drying temperature is a solvent having a boiling point below that of ethanol.

7. A method as claimed in claim 6 wherein the solvent in the solvent mixture for the active ingredient with a boiling point below the drying temperature is methanol.

8. A method as claimed in claim 1 wherein the solvent mixture for the active ingredient comprises at least one solvent having a boiling point above the drying temperature selected from the group consisting of diethylene glycol, propylene glycol, propylene carbonate, glycerol, lower molecular weight polyethylene glycols, propylene glycol esters, polyol fatty acid esters, fatty alcohol derivatives, oleic acid, iso-octyl stearate, isopropyl myristate, isopropyl palmitate, ethyl oleate, di-isopropyl adipate, diethylsuccinate, hexylaurate, triglycerides of caprylic or capric acids, diethyl toluamide, laurocapram, n-methylpyrrolidone, diethylene glycol monoethyl ether and essential oils.

9. A method as claimed in claim 1 wherein the drying step (c) is carried out at or above 100° C.

10. A method as claimed in claim 1 wherein the drying step (c) is carried out at a temperature below the boiling point of ethanol.

11. A method as claimed in claim 1 wherein the active ingredient comprises at least one active agent selected from the categories antihistamines, steroid hormones, progestins, vasodilators, antihypertensives, bronchodilators, anti-tumor agents, alkaloids and analgesics.

12. A method as claimed in claim 1 wherein the film prepared in step (b) is formed by coating the mixture prepared in step (a) onto a thin flexible sheet material.

13. A method as claimed in claim 12 wherein the thin flexible sheet material is a siliconised release liner.

14. A method as claimed in claim 12 wherein the flexible sheet material is a backing material impermeable to the active ingredient.

15. A method as claimed in claim 12 wherein the film formed in step (b) is between 5 $\mu$m and 500 $\mu$m thick.

16. A method as claimed in claim 13 wherein the coated surface of the release liner is laminated to a backing material impermeable to the active ingredient.

17. A method as claimed in claim 14 wherein the coated surface of the impermeable backing material is laminated to a siliconised release liner.

18. A method as claimed in claim 13 wherein the coated surface of the release liner is laminated to a rate control membrane the free surface of which is further coated with the mixture prepared in step (a).

19. A method as claimed in claim 14 wherein the coated surface of the backing material is laminated to a rate control membrane, the free surface of which is further coated with the mixture prepared in step (a).

20. A method as claimed in claim 18 wherein the coated rate control membrane is laminated to a further rate control membrane or to a backing material impermeable to the active ingredient.

21. A method as claimed in claim 18 wherein the coated rate control membrane is laminated to a further rate control membrane or to a siliconised release liner.

22. A method as claimed in claim 18 wherein the thickness of the adhesive/active ingredient layer on either side of the rate control membrane is varied to control the rate of migration across the membrane.

23. A method as claimed in claim 19 wherein the thickness of the adhesive/active ingredient layer on either side of the rate control membrane is varied to control the rate of migration across the membrane.

24. A method as claimed in claim 18 wherein the thickness of the adhesive/active ingredient layer on either side of the rate control membrane is varied to control the proportion or amount of active ingredient immediately available adjacent to the skin for absorption.

25. A method as claimed in claim 19 wherein the thickness of the adhesive/active ingredient layer on either side of the rate control membrane is varied to control the proportion or amount of active ingredient immediately available adjacent to the skin for absorption.

26. A method as claimed in claim 14 wherein the backing material impermeable to the active ingredient is selected from the group consisting of a polyester film laminate, metalised polyester laminate co-extruded high barrier film and an air and water permeable polyurethane.

27. A method as claimed in claim 18 wherein the rate control membrane is selected from the group consisting of polypropylene film, a polyvinyl acetate film and an ethylvinyl acetate film.

28. A method as claimed in claim 19 wherein the rate control membrane is selected from the group consisting of polypropylene film, polyvinyl acetate film and ethylvinyl acetate film.

29. A device for transdermal delivery of an active ingredient prepared by the method as claimed in claim 1.

* * * * *